United States Patent [19]
Olweus et al.

[11] Patent Number: 6,008,004
[45] Date of Patent: Dec. 28, 1999

[54] IDENTIFICATION OF A CD34+ BONE MARROW PRECURSOR FOR DENDRITIC CELLS IN BLOOD AND LYMPHOID TISSUES

[75] Inventors: Johanna Olweus; Fridtjof Lund-Johansen, both of Kristiansand, Norway

[73] Assignee: Becton Dickinson & Company, Franklin Lakes, N.J.

[21] Appl. No.: 08/939,545

[22] Filed: Sep. 29, 1997

Related U.S. Application Data

[60] Provisional application No. 60/027,898, Oct. 4, 1996.
[51] Int. Cl.⁶ ............................. G01N 33/53; C12N 5/08; C07K 16/28
[52] U.S. Cl. ............................. 435/7.24; 435/2; 435/325; 435/355; 435/372; 436/824; 530/388.22
[58] Field of Search ............................. 435/7.24, 2, 355, 435/372, 325; 436/824; 530/388.22

[56] References Cited

FOREIGN PATENT DOCUMENTS

| 0 563 485 A1 | 10/1993 | European Pat. Off. . |
| WO 95/28479 A1 | 10/1995 | WIPO . |

OTHER PUBLICATIONS

O'Doherty, U. et al., "Human Blood Contains Two Subsets of Dendritic Cells, One Immunologically Mature and the Other Immature," *Immunology*, 82:487–493, 1994.

Olweus, J. et al. Immunomethods 5: 179–188, 1994.

Galy, A. et al. Immunity 3: 459–473, Oct. 1995.

Santiago–Schwarz, F. et al. Blood 82(10): 3019–3028, Nov. 1993.

C. Caux et al.: "Interleukin–3 cooperates with tumor necrosis factor alpha for the development of human dendritic_Langerhans cells from cord blood CD34+ hematopoietic progenitor cells." Blood, vol. 87, No. 6, Mar. 15, 1996, New York, NY, USA, pp. 2376–2385, XP002052034 See the whole document.

B. Herbst et al.: "In vitro differentiation of CD34+ hematopoietic progenitor cells toward distinct dendritic cell subsets of the birbeck granule and MIIC–positive Langerhans cell and the interdigitating dendritic cell type." Blood vol. 88, No. 7, Oct. 1, 1996, New York, NY, USA, pp. 2541–2548, XP002052035 see the whole document.

W. Egner et al.: "The phenotype of freshly isolated and cultured human bone marrow allostimulatory cells: possible heterogeneity in bone marrow dendritic cell populations." Immunology, vol. 85, No. 4, Aug. 1995, Oxford, GB, pp. 611–620, XP000608115 see abstract.

*Primary Examiner*—Christina Y. Chan
*Assistant Examiner*—F. Pierre VanderVegt
*Attorney, Agent, or Firm*—Fish & Neave; Daniel M. Becker; Vicki S. Veenker

[57] ABSTRACT

Dendritic cells (DCs) are the primary antigen presenting cells during the initiation of T cell-dependent immune responses. The cells originate from the bone marrow and have been suggested to represent a distinct cell lineage. However, distinct DC precursors have not been identified in bone marrow, and mature monocytes can also give rise to DCs. The instant invention presents a distinct DC precursor among bone marrow CD34+ cells. The cells express high levels of the interleukin-3 receptor a chain and CD4 and can be uniquely identified also in blood and lymphoid tissues by this phenotype.

11 Claims, 8 Drawing Sheets

FIG-4A Adult Tonsil

FIG-4B Fetal Lymph Node

IDENTIFICATION OF A CD34+ BONE MARROW PRECURSOR FOR DENDRITIC CELLS IN BLOOD AND LYMPHOID TISSUES

CROSS-REFERENCE TO RELATED APPLICATIONS

This application claims the benefit of U.S. Provisional Application Ser. No. 60/027,898, filed Oct. 4, 1996.

BACKGROUND OF INVENTION

Dendritic cells (DCs) play a key role in the immune system as initiators of primary T cell responses. DCs are difficult cells to isolate because they are sparsely distributed in the tissues, and because there is a lack of positive markers identifying the cells. There is, thus, little information concerning DCs in various organs, and, while various researchers have postulated on the origin of these cells, it is not definitively known whether these cells constitute a separate lineage of cells. Furthermore, while there are many theories regarding this, it is not known if there is a dendritic committed progenitor cell in the bone marrow. The importance of solving these questions has become evident from a clinical perspective, as their function has made them into critical targets for vaccine development against tumor cells, and, potentially, in the development of vaccines against HIV-infection.

Furthermore, since some DCs have been observed to serve as reservoirs for the HIV-virus, identification of subtypes of cells having differences in infectability potential and/or the ability to provide infection resistance, is becoming increasingly desirable. In addition, there is considerable interest in identifying subsets of DCs believed to be involved in the induction of donor-specific tolerance after transplantation. Thus, there exists a need for methodologies to characterize isolate dendritic cells.

Such methodologies would also be useful in the isolation of DCs by utilization of the phenotype by use of cytometry. Flow cytometry is particularly useful in this regard, as the cells bearing a particular phenotype can be recognized and sorted by use of labeled antibodies. Thus, DCs of a known phenotype could be sorted and isolated.

SUMMARY OF INVENTION

Figure 1A:
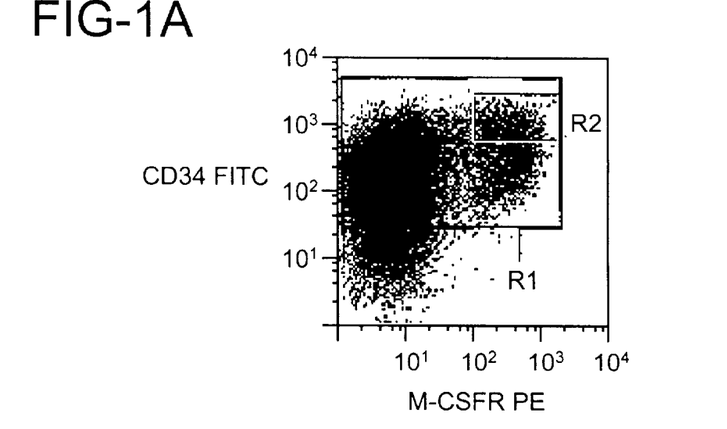
Figure 1B:
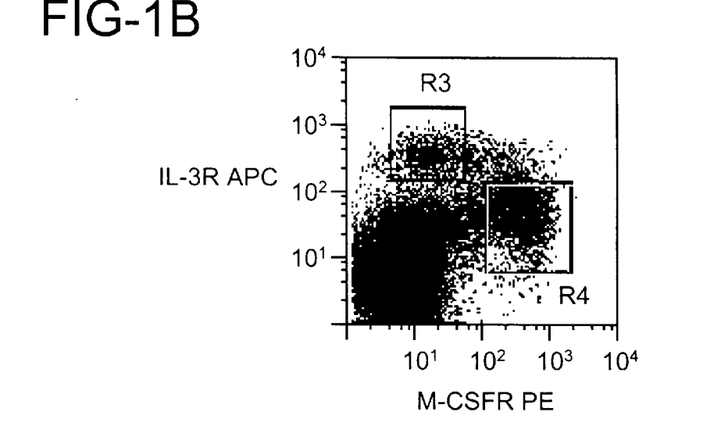
Figure 1C:
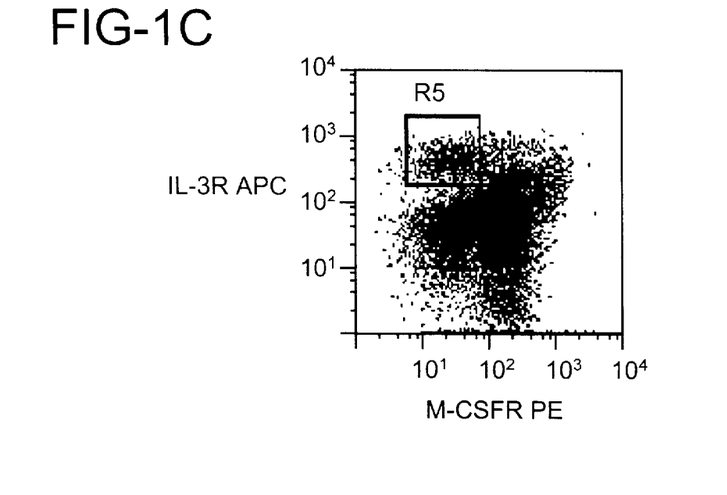
Figure 1D:
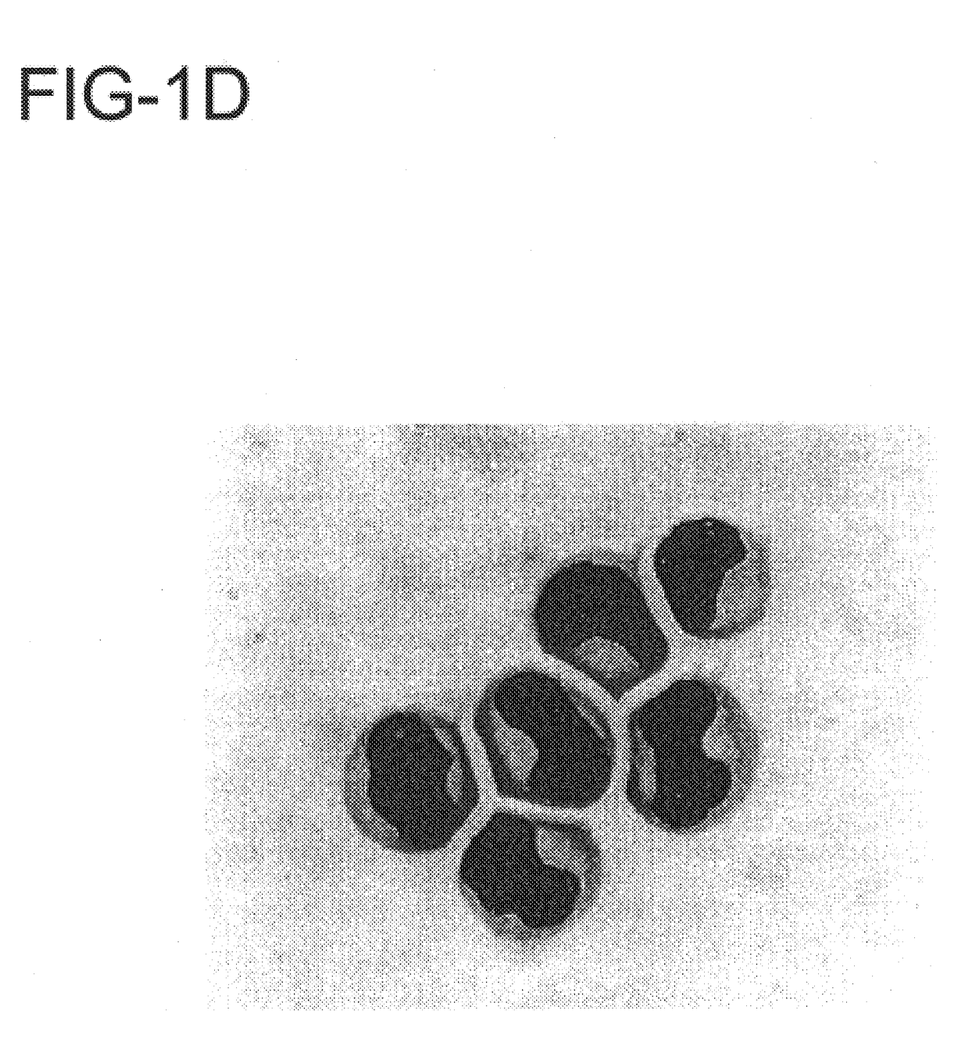
FIG. 1D presents a micrograph of these cells.

A CD34+ (as used herein, any cell designated as positive (+) for a particular marker will be a cell which expresses that marker as evidenced by the binding of an antibody directed against the recited marker; a cell designated as negative (−) does not express the marker as measured by the same methodology) mammalian, preferably human, bone marrow precursor of a distinct type of DCs that can be identified in peripheral blood, thymus, spleen, tonsil and lymph nodes solely by the positive expression of CD123 and CD4 has been characterized. This CD34+ population of bone marrow cells contains primitive progenitor cells capable of reconstituting the entire hematopoietic system and more differentiated progenitors committed to a single lineage. Subsets of progenitor cells can be identified by specific cell surface markers. It is known that the receptor for macrophage-colony-stimulating factor (M-CSFR/CD115) is expressed on granulomonocytic progenitors, but not on primitive, erythroid, or CD19+ B-lymphoid progenitors. A population of CD34lo (as used herein, the magnitude of expression of a particular antigen can be designated as lo or hi; such cells express the antigen, as measured by the binding of an antibody directed against the recited antigen, to a lesser (for lo) or greater (for hi) magnitude than at least 50%, preferably 75%, more preferably 90% of the cells which are positive for the recited antigen) cells (3±0.8% of the CD34+ cells) was identified that stained brightly with antibodies to the interleukin 3 receptor alpha chain (IL3R alpha/CD123) and weakly with antibodies to the M-CSFR (see FIG. 1A, B). Similar cells could be generated by short term culture of M-CSFR+ cells, suggesting that the cells belong to the granulomonocytic lineage (see FIG. 1C). Unlike most granulomonocytic progenitors in fetal bone marrow, the CD123hi cells had low levels of CD64 and CD13, but expressed high levels of CD36, a molecule found on monocytic cells. Further characterization showed that the cells had several phenotypic characteristics of DCs precursors isolated from peripheral blood (CD3−, CD4+, CD11−, CD13lo, CD14−, CD16−, CD19−, CD33+, CD45RA+, CD45RO−, CD56−, CD64−, HLA-DR+). Morphologically the cells had a smooth plasma membrane, abundant agranular cytoplasm and reniform or slightly lobulated nucleus (see FIG. 1 D).

BRIEF DESCRIPTION OF THE FIGURES

FIGS. 1A–1D presents dot plots of CD34 (FIG. 1A) and IL-3R alpha (FIGS. 1B and 1C) versus M-CSFR expression (FIGS. 1A–1C) of isolated CD34lo CD123hi cells.

DETAILED DESCRIPTION OF INVENTION

Figure 2A:
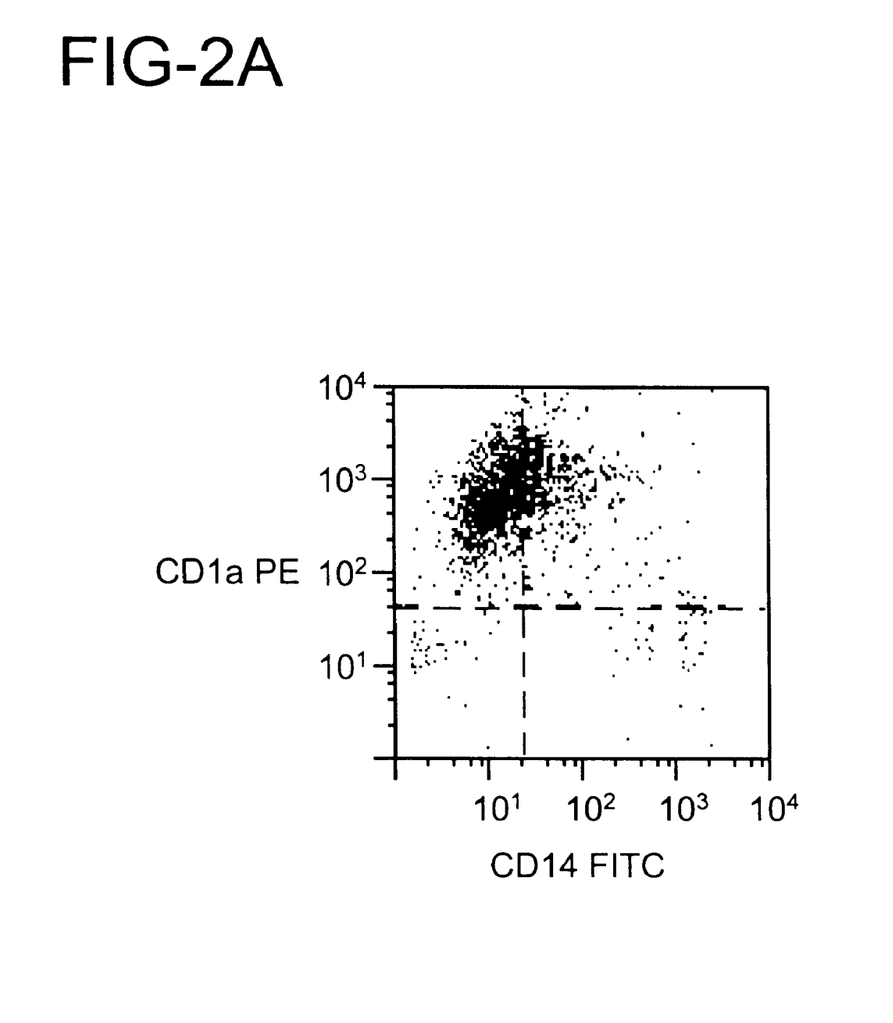
FIG. 2A presents a dot plot of CD1a versus CD 14 expression of CD34lo CD123hi cells cultured for 7 days.

To examine the developmental potential of CD34+ CD123hi cells, the cells were sorted using a flow cytometer and fluorescently labeled antibodies using techniques well-known in the art, and cultured with a wide range of cytokines capable of supporting multiple hematopoietic lineages [granulocyte-macrophage colony-stimulating factor (GM-CSF), G-CSF, M-CSF, interleukin-3 (IL-3), IL-6, stem cell factor (SCF) and erythropoietin (Epo)]. Cells from freshly isolated bone marrow and those generated in vitro from CD34hi CD115+ cells gave similar results, but the viability was better for the latter. Sorted cells rapidly formed large aggregates after few hours in liquid culture, a growth pattern which is characteristic of DCs. After 7 days the cells were positive for the DC marker CD1a, whereas markers for monocytes (CD14) and granulocytes (CD15) were absent or expressed at low density (see FIG. 2A). Wright-Giemsa-stained cytospin preparations showed that the cells had abundant, agranular, cytoplasm with dendritic protrusions, and round nuclei. The CD34+ CD123hi cells expanded on average only 3-fold during this culture period, and no further cell expansion occurred between 7 and 20 days of culture under these conditions.

Figure 2B:
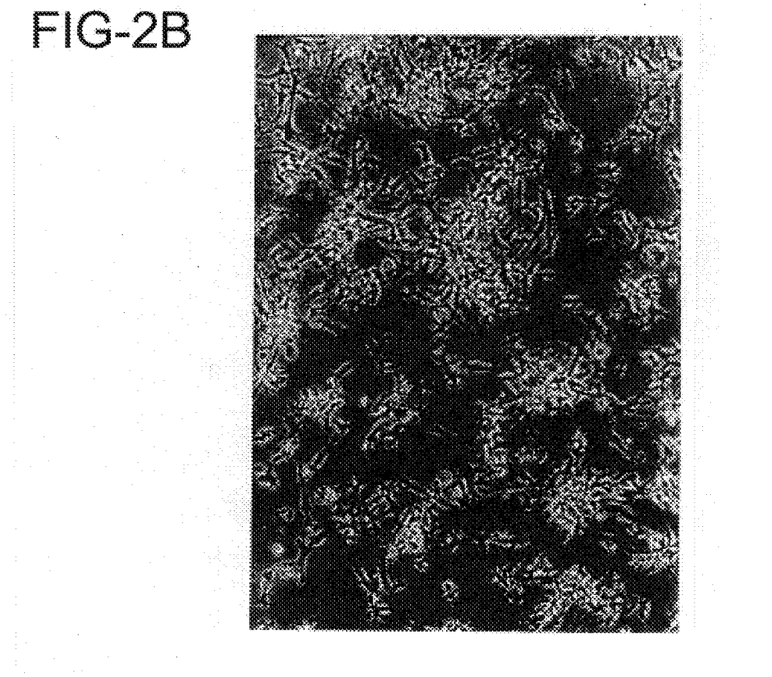
FIGS. 2B and 2C present micrographs of these cells cultured only in the presence of GM-CSF.
Figure 2C:
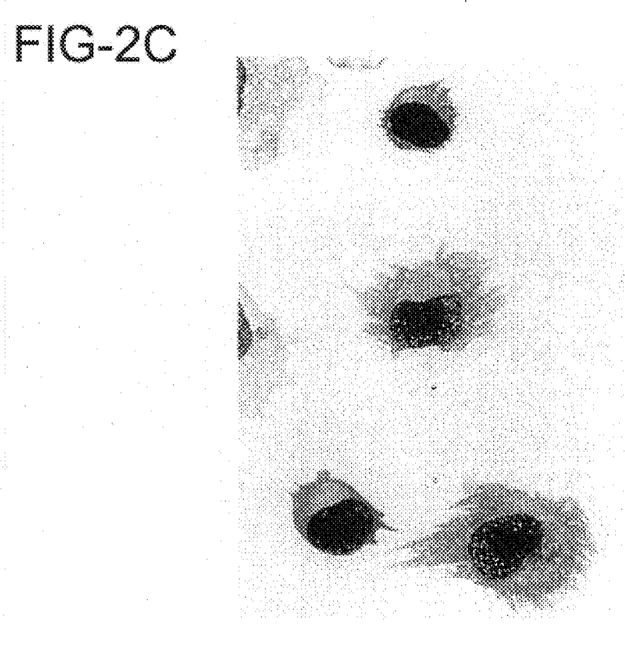
Figure 2D:
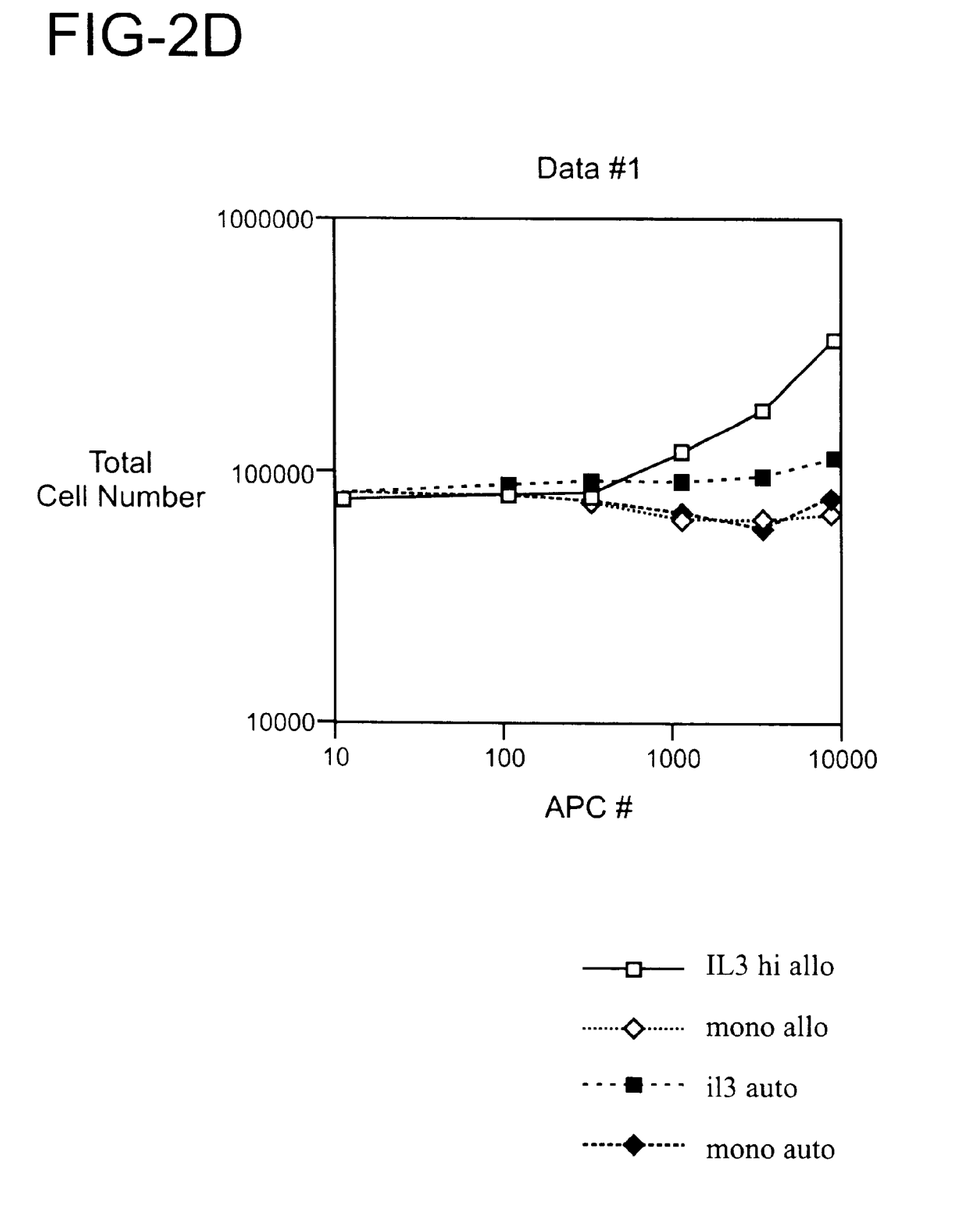
FIG. 2D demonstrates the reactivity of these cells as activators of CD4+ allogenic T-cells.
Figure 2E:
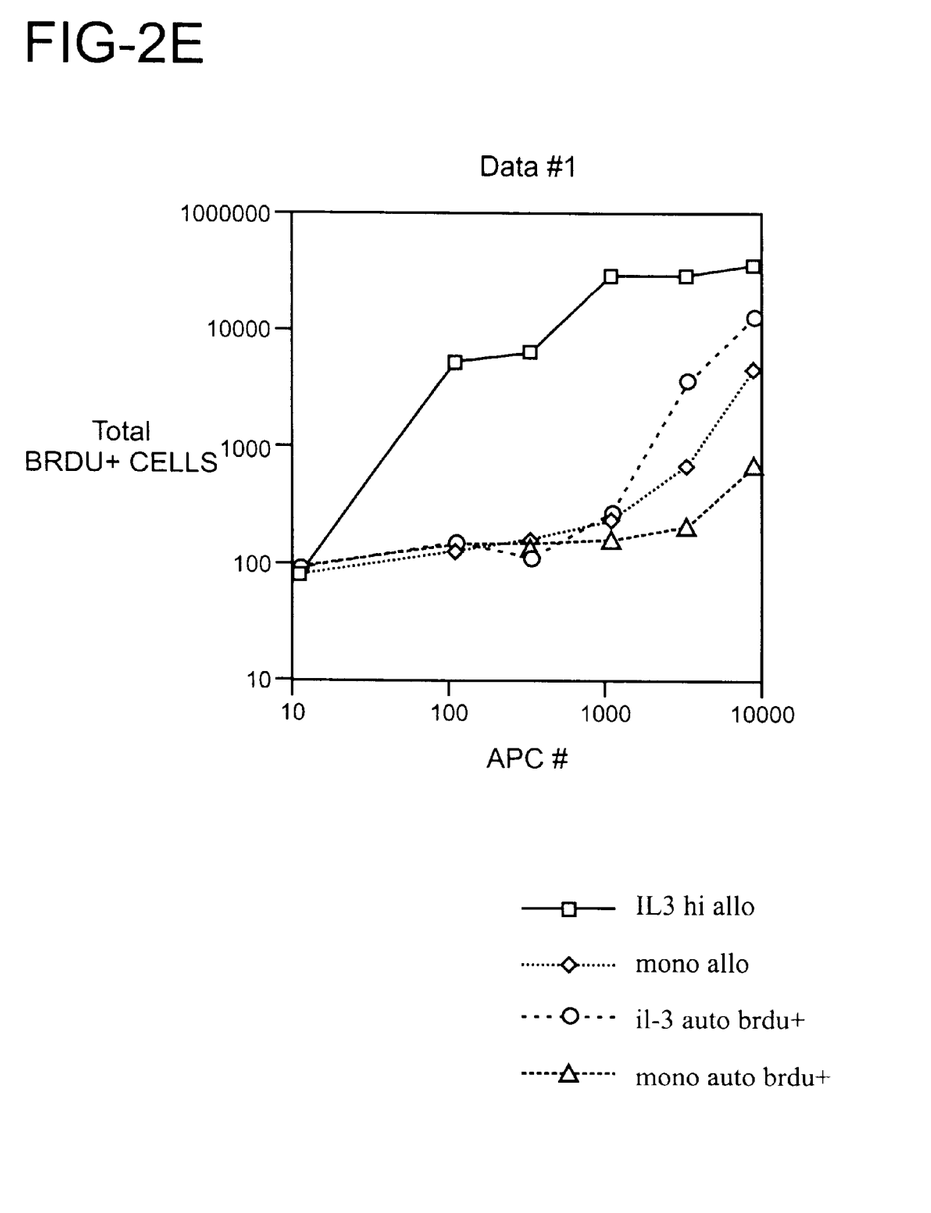

The expression of CD1a could indicate that the cells were DCs of the Langerhans type. However, electron microscopy of freshly isolated and resorted CD34+ CD123hi cells cultured 7 days in GM-CSF and TNF alpha generated cells lacking Birbeck granules, but with a dendritic morphology of lobulated nucleus and a villous surface. The CD34+ CD123hi cells assumed dendritic morphology also when cultured with GM-CSF as the only added cytokine (see FIG. 2B, C), and expressed high levels of HLA-DR and the costimulatory molecule CD80. These cells were potent activators of allogeneic CD4+ T cells compared to macrophages (see FIG. 2D).

Figure 3A:
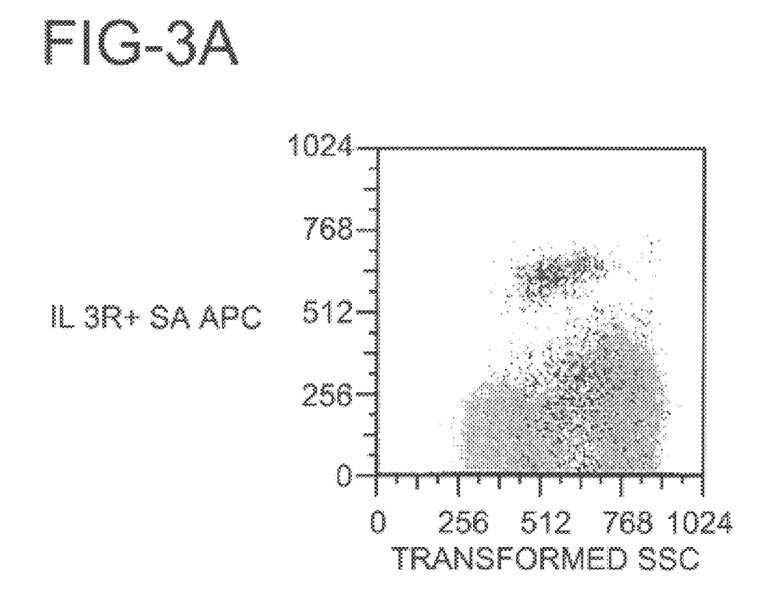
FIGS. 3A–3B presents dot plots of side scatter versus CD123 expression (FIG. 3A) and HLA-DR expression (FIG. 3B).
Figure 3B:
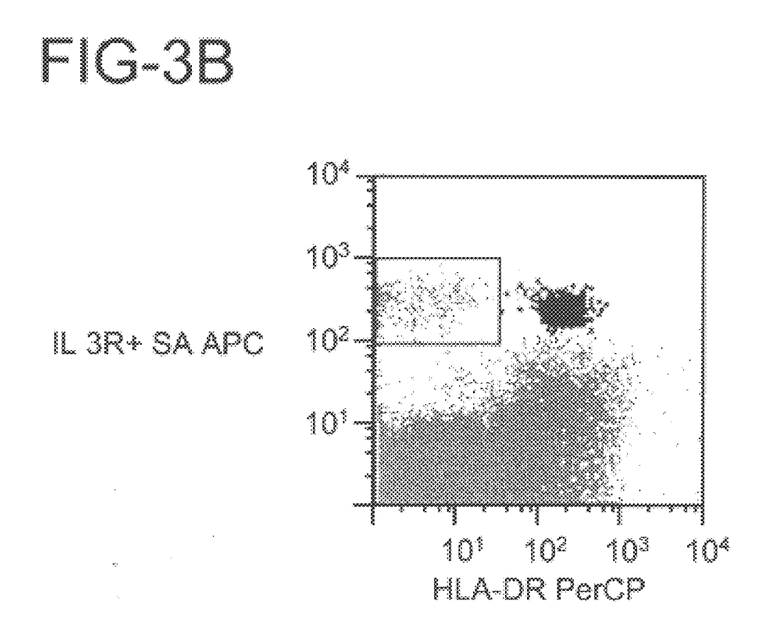

A distinct population of CD123hi cells was also observed among peripheral blood mononuclear cells (see FIG. 3A). Among these, 60% were negative for HLA-DR and CD4 (within region in FIG. 3B), positive for anti-human IgE and CD11b and had morphological characteristics of basophilic granulocytes. However, 40% expressed high levels of molecules typically expressed by DCs, such as CD4, HLA-DR (MHC class II) (see FIG. 3B), the costimulatory molecules CD40 and CD86 and the adhesion molecules CD54 (ICAM-1) and CD58, but with low or negative expression of the costimulatory molecule CD80. The cells furthermore expressed the DC-associated marker CMRF-44, and had almost identical immunophenotype to the CD34+ CD123hi cells (CD3−, CD11b−, CD11c−, CD13lo, CD14−, CD15−, CD16−, CD19−, CD33lo, CD45RA+, CD45RO, CD56−, CD64−). The CD123hi CD4+ cells had agranular cytoplasm and a reniform or lobulated nucleus, similar to the CD34+ CD123hi cells. In culture, the cells formed large aggregates similar to those observed during culture of bone marrow cells. When allowed to differentiate for 36h in culture, the CD123hi HLA-DR+ cells induced extensive proliferation of both allogeneic and autologous T cells compared to monocytes. The cells therefore have similar morphology, phenotype and functional characteristics as a population of peripheral blood DCs described in several earlier publications. Our results provide evidence to support the hypothesis from those studies that these DCs represent immature cells in transit from bone marrow to tissues.

In addition to the population described above, peripheral blood contains several other cell types that can give rise to DCs in vitro, including CD34+ cells, mature monocytes and a population of HLA-DRhi CD11hi cells that express low levels of a number of lineage markers for B cells, T cells, NK cells, and monocytes. The relationship between each population and DCs in various tissues has been difficult to establish, as several DCs change phenotypic characteristics during migration. Cell tracking experiments in rats have, however, shown that some immature DCs rapidly migrate via blood and lymphatics to T cell-dependent areas of secondary lymphoid tissue. While not wishing to be bound by theory, it is hypothesized that CD123hi CD4+ cells may have a similar migratory pathway and enter tonsils and spleen with little changes in phenotype.

Figure 4A:
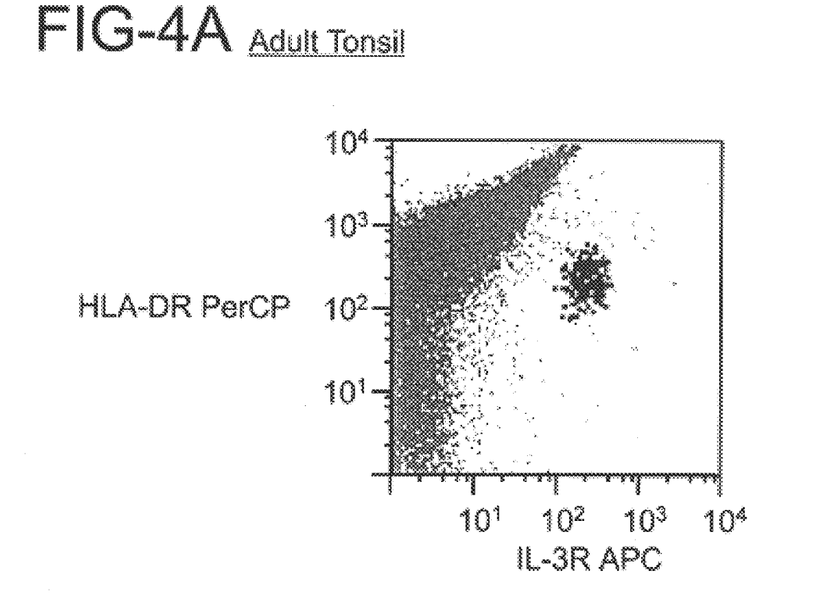
FIGS. 4A–4B presents dot plots of CD123 expression versus HLA-DR expression for adult tonsil (FIG. 4A) and fetal lymph node (FIG. 4B) derived cells.

Tonsillar DCs were identified as cells with high expression of HLA-DR and low levels of lineage markers for B cells, T cells, NK cells and monocytes. Cells with these characteristics constituted 0.2–0.4% of the total mononuclear cell population, and interestingly the majority were CD123hi CD4+ HLA-DR+ (see FIG. 4A). Tonsillar CD123hi cells were also uniformly CD4+ and had an immunophenotype similar to that of blood CD123hi cells. This phenotype is also compatible with that shown for tonsillar DCs in previous reports. An important difference between blood and tonsillar cells was, however that tonsillar CD123hi cells had almost undetectable levels of L-selectin. The cells shared the growth pattern of CD123+CD4+ cells from bone marrow and blood.

On sections, CD123 bright cells were found scattered throughout the extrafollicular areas, suggesting that these cells might be DCs of the interdigitating type. A similar staining pattern was observed for CD36, which specifically identified DCs in preparations of mononuclear cells. CD1 23 also stained endothelium, but these cells are CD4−. The CD123hi CD4+ cells were also found at low frequencies (0.1–0.2%) in adult spleen.

Figure 4B:
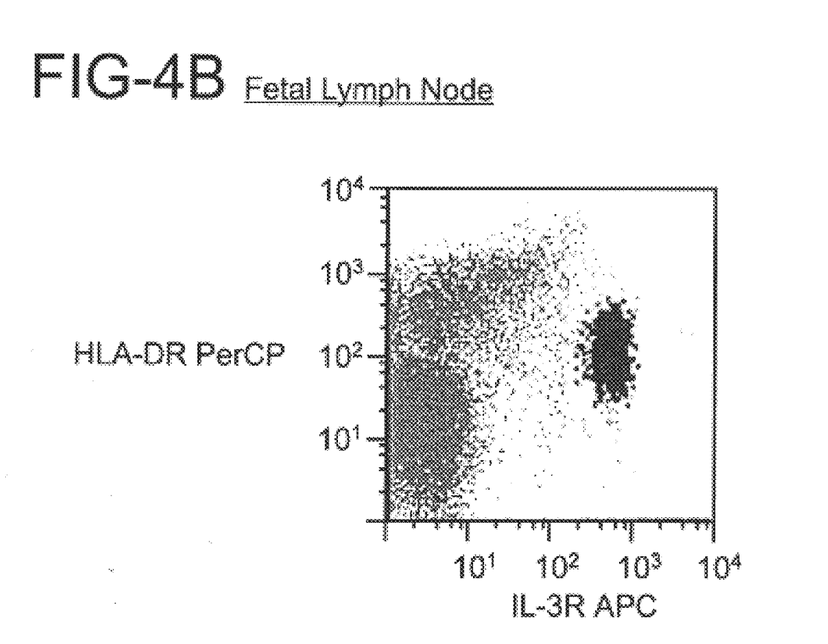

Dendritic cells may play an important role in the development of lymph nodes as mice deficient in Rel B lack DCs and are deficient in lymph nodes. An analysis of human fetal lymph nodes for the presence of CD123hi CD4+ cells was therefore conducted. In agreement with the hypothesized function in lymph node development, we found a high percentage (3–4%) of CD123hi CD4+ HLA-DR+ cells in fetal lymph nodes (FIG. 4B). The frequency of thymic CD123hi CD4+ cells was, however, low, constituting 0.2–0.3% of the mononuclear cells.

Thus, a population of interleukin-3 receptorhi (CD123hi) CD4+ CD34+ bone marrow progenitor cells of myeloid origin differentiate into dendritic cells. Interleukin-3Rhi CD4+ cells with highly similar characteristics to the bone marrow population, are furthermore readily detected among freshly isolated mononuclear cells from peripheral blood, tonsil, thymus, adult and fetal lymph nodes. The frequencies were particularly high in fetal lymph nodes, suggesting an important role in the ontogeny of lymphoid tissues. The possibility to identify and link the identity of dendritic cells in blood, bone marrow and lymphoid tissues should facilitate the understanding of the role of dendritic cells in normal and pathological regulation of the immune system.

It is apparent that many modifications and variations of this invention as hereinabove set forth may be made without departing from the spirit and scope thereof The specific embodiments described are given by way of example only, and the invention is limited only by the terms of the appended claims.

What is claimed is:

1. A method of enriching for TNFα-independent dendritic cell precursors in a population containing CD34$^+$ cells, comprising the steps of:

contacting said population with an anti-CD123 antibody; and then selecting the cells that are CD34$^+$CD123$^+$.

2. The method of claim 1, wherein said anti-CD123 antibody is detectably labeled.

3. The method of claim 2, wherein said label is fluorescent.

4. The method of claim 3, wherein said selection is flow cytometric selection.

5. The method of claim 3, wherein said label is selected from the group consisting of FITC, APC, PerCP, and PE.

6. The method of claim 1, wherein said cell population is freshly isolated from bone marrow.

7. A method of distinguishing TNFα-independent dendritic cell precursors within a population of CD34$^+$ dendritic cell precursors, comprising the steps of:

contacting said population with an anti-CD123 antibody; and then detecting the cells that are CD34$^+$CD123$^+$.

8. The method of claim 7, wherein said anti-CD123 antibody is detectably labeled.

9. The method of claim 8, wherein said label is fluorescent.

10. The method of claim 9, wherein said detection is flow cytometric detection.

11. The method of claim 9, wherein said label is selected from the group consisting of FITC, APC, PerCP, and PE.

* * * * *